United States Patent [19]

Osterholm

[11] Patent Number: 4,840,617

[45] Date of Patent: Jun. 20, 1989

[54] CEREBRAL AND LUMBAR PERFUSION CATHETERIZATION APPARATUS FOR USE IN TREATING HYPOXIC/ISCHEMIC NEUROLOGIC TISSUE

[75] Inventor: Jewell L. Osterholm, Radnor, Pa.

[73] Assignee: Thomas Jefferson University, Philadelphia, Pa.

[21] Appl. No.: 238,982

[22] Filed: Aug. 24, 1988

Related U.S. Application Data

[60] Continuation of Ser. No. 755,427, Jul. 16, 1985, abandoned, which is a continuation-in-part of Ser. No. 428,900, Sep. 30, 1982, Pat. No. 4,758,431, and a continuation-in-part of Ser. No. 582,961, Feb. 23, 1984, Pat. No. 4,686,085, which is a division of Ser. No. 428,850, Sep. 30, 1982, Pat. No. 4,445,500, said Ser. No. 428,900, and Ser. No. 428,850, each is a division of Ser. No. 354,346, Mar. 3, 1982, Pat. No. 4,445,886, which is a continuation-in-part of Ser. No. 139,886, Apr. 14, 1980, Pat. No. 4,378,797.

[51] Int. Cl.$^4$ .................. A61M 25/02; A61M 5/00; A61M 1/00; A61B 19/00
[52] U.S. Cl. ...................... 604/174; 128/DIG. 26; 128/303 R; 604/119
[58] Field of Search .................. 604/174–179; 128/327, DIG. 26, 303

[56] References Cited

U.S. PATENT DOCUMENTS

| | | | |
|---|---|---|---|
| 2,571,461 | 10/1951 | Livingston et al. | 128/327 |
| 2,616,429 | 11/1952 | Merenlender | 128/350 |
| 2,670,730 | 3/1954 | Kellogg | 128/2 |
| 3,017,887 | 1/1962 | Heyer | 128/303 B |
| 3,135,263 | 6/1964 | Connelley, Jr. | 128/303 B |
| 3,233,610 | 2/1966 | Wade | 604/247 X |
| 3,357,431 | 12/1967 | Newell | 128/303 B |
| 3,457,922 | 7/1969 | Ray | 128/303 |
| 3,482,575 | 12/1969 | Claff et al. | 128/214 |
| 3,516,410 | 6/1970 | Hakim | 128/350 |
| 3,583,387 | 6/1971 | Garner | 128/1 |
| 3,626,950 | 12/1971 | Schulte | 128/350 |
| 3,669,094 | 6/1972 | Heyer | 128/2 |
| 3,669,116 | 6/1972 | Heyer | 128/350 |
| 3,690,323 | 9/1972 | Wortman et al. | 128/350 |
| 3,753,865 | 8/1973 | Belzer | 195/127 |
| 3,818,229 | 6/1974 | Long, Jr. | 250/312 |
| 3,823,091 | 7/1974 | Samejima | 252/312 |
| 3,889,687 | 6/1975 | Harris et al. | 604/247 X |
| 3,894,541 | 7/1975 | El-Shafei | 128/350 |
| 3,924,635 | 12/1975 | Hakim | 604/247 X |
| 3,938,530 | 2/1976 | Santomieri | 128/349 |
| 3,941,119 | 3/1976 | Corrales | 128/2 |
| 3,946,731 | 3/1976 | Lichtenstein | 128/214 |
| 3,975,512 | 8/1976 | Long, Jr. | 424/5 |
| 3,989,843 | 11/1976 | Chabert et al. | 424/325 |
| 4,073,879 | 2/1978 | Long, Jr. | |
| 4,110,474 | 8/1978 | Lagow et al. | 424/350 |
| 4,148,314 | 4/1979 | Yin | 128/214 |
| 4,163,734 | 4/1979 | Sorensen et al. | 252/408 |

(List continued on next page.)

FOREIGN PATENT DOCUMENTS

| | | |
|---|---|---|
| 4127178 | 11/1978 | Australia . |
| 4295478 | 12/1978 | Australia . |
| 5451380 | 1/1980 | Australia . |
| 6255580 | 9/1980 | Australia . |
| 973094 | 8/1985 | Canada . |
| 2911912 | 10/1980 | Fed. Rep. of Germany . |
| 2163191 | 7/1982 | Fed. Rep. of Germany . |
| 2118977 | 7/1975 | France . |
| 1381879 | 5/1975 | United Kingdom . |

OTHER PUBLICATIONS

Bose, B. et al., "Focal Cerebral Ischemia: Reduction in Size of Infarcts by Ventriculo–Subarachnoid Perfusion with Fluorocarbon Emulsion", Brain Research, 328 (7/1985), 223–231.

Primary Examiner—Nancy A. B. Swisher
Attorney, Agent, or Firm—Woodcock Washburn Kurtz Mackiewicz & Norris (List continued on next page.)

[57] ABSTRACT

A cerebral catheterization apparatus for delivering oxygenated nutrient to or from the cerebro-spinal fluid pathway of a patient suspected of suffering from ischemic central nervous system tissue is disclosed. The apparatus comprises catheter means for providing a delivery pathway for an oxygenated nutrient to the lateral ventricle of the brain, which delivery pathway comprises an inlet and outlet; guide means, mating with the catheter means, for directing the catheter means toward the lateral ventricle; and a harness, on which the guide means is mounted, which is positionable with respect to the patient's head such that the catheter means may be reliably inserted into the lateral ventricle.

21 Claims, 3 Drawing Sheets

U.S. PATENT DOCUMENTS

| | | | |
|---|---|---|---|
| 4,173,224 | 11/1979 | Marx et al. | 128/214 |
| 4,173,654 | 11/1979 | Scherer | 424/350 |
| 4,228,799 | 10/1980 | Anichkor et al. | 128/303 B |
| 4,314,513 | 2/1982 | Nawash et al. | 128/348 |
| 4,373,797 | 4/1983 | Osterholm | 604/24 |
| 4,393,863 | 7/1983 | Osterholm | 128/1 R |
| 4,393,873 | 7/1983 | Nawash et al. | 604/174 X |
| 4,423,077 | 12/1983 | Sloviter | 424/325 |
| 4,443,480 | 4/1984 | Clark, Jr. | 424/352 |
| 4,445,500 | 5/1984 | Osterholm | 128/1 R |
| 4,445,514 | 5/1984 | Osterholm | 128/632 |
| 4,445,886 | 5/1984 | Osterholm | 604/28 |
| 4,445,887 | 5/1984 | Osterholm | 604/28 |
| 4,445,888 | 5/1984 | Osterholm | 604/28 |
| 4,446,154 | 5/1984 | Osterholm | 424/350 |
| 4,446,155 | 5/1984 | Osterholm | 424/350 |
| 4,450,841 | 5/1984 | Osterholm | 128/632 |
| 4,451,251 | 5/1984 | Osterholm | 604/28 |
| 4,500,311 | 2/1985 | Redmond et al. | 604/246 |
| 4,516,968 | 5/1985 | Marshall et al. | 604/174 |
| 4,613,324 | 9/1986 | Ghajar | 604/49 |

OTHER PUBLICATIONS

Brochure for the H-1500 Elliptical Oxygenator-Harvey Cardiopulmonary Div. of C. R. bard, Inc., 6/86.

Siegel et al., *Basic Neurochemistry*, 2d Little Brown Boston (6/1978), p. 297.

Rodnight, R:, *Biochemistry Journal*, vol. 57, p. 661, 5/86.

Clark et al., *Science*, vol. 152, pp. 1755-1756 (5/1966).

Gollon, F. et al., *Alabama Journal of Medical Science*, vol. 4, p. 336 (5/1967).

Gollon, F. et al., *The Physiologist*, vol. 9, p. 191 (5/1966).

Sloviter, H. A. et al., *Nature* (London), vol. 216, p. 458 (5/1967).

Geyer, R. P. *Federation Proceedings*, vol. 29, No. 5, Sep.-Oct. 4, 1970.

Geyer, R. P., Med u Ernohn, vol. 11, p. 256 (4/1970).

Krone, W. et al., *Biochemika et Biophysica Acta*, vol. 372, pp. 55-71 (4/1974).

Rosenblum, W. I., "Fluorocarbon Emulsions and Cerebral Microcirculation," *Federation Proceedings*, vol. 34, No. 6, p. 1493 (May, 1975).

Kontos, H. A. et al., "Role of Tissue Hypoxemia in Local Regulation of Cerebral Microcirculation," *American Journal of Physiology*, vol. 363, pp. 582-591 (5/1978).

Hare et al., "Rapid and Sensitive Ion-Exchange Fluorometric Measurement of G-Aminobutyric Acid in Physiological Fluids", Anal. Biochem, vol. 101, pp. 349-355 (4/1980).

Navari et al., *Res. Exp. Med.*, vol. 170, pp. 169-180 (4/1977).

Clark et al., *Fed. Proc.*, vol. 34, pp. 1468-1477 (3/1979).

Osterholm, J. L., *Pathophysiology of Spinal Cord Injury*, C. C. Thomas, Springfield, Illinois (3/1978).

Pappenheimer, J. R. et al., "Perfusion of the Cerebral Ventricular System in Unanesthized Goats," *Am. J. Physiol.*, vol. 203, No. 5, pp. 763-774 (3/1962).

Curtis, C. "Blood and Money", *Forbes*, pp. 100-102 (Nov. 9, 2/1981).

Dirks, et al., "Fluorocarbon Perfusion Medium Applied to the Isolated Rat Brain", *Journal of Pharmacological Methods* 4:95-108 (2/1980).

Fischer et al., "Reassessment of Cerebral Capillary Changes in Acute Global Ischemia and Their Relationship to the 'No-Reflow Phenomenon'", *Stroke*, vol. 8, pp. 36-39 (2/1977).

Carey, et al., "The Effect of Severe Hypoglycemia Upon Cerebrospinal Fluid Formation, Ventricular Iodide Clearance, and Brain Electrolytes in Rabbits", *J. Neurosurg.*, Vo. 54, pp. 370-379 (2/1981).

Chiang, et al., "Cerebral Ischemia: Vascular Changes", *American Journal of Pathology*, Vo. 52, pp. 455-476, (2/1968).

Clark et al., "Can Fluorocarbon Emulsions be Used as Artifical Blood?" *Triangle*, vol. 11, No. 4, pp. 115-122 (2/1972).

Britton et al., "Effect of Cerebral Extracellular Fluid Acidity on Total and Regional Cerabral Blood Flow", *Journal of Applied Phys.*, vol. 47, pp. 818-826, Oct.-Dec. (1979).

Brown et al., "Fluorocarbon Sonicated as a Substitute for Erythrocytes in Rat Liver Perfusion", *Surgery*, Vo. 71, No. 3, pp. 388-394 (Mar., 1972).

Callaghan, et al., "CSF Perfusion to Treat Intraventricular Penicillin Toxicity", *Arch. Neurol.*, vol. 38, pp. 390-391 (1/1981).

Astrup, et al., "The Increase in Extravellular Potassium Concentration in The Ischemic Brain in Relation to the Preischemic Functional Activity and Cerebral Metabolic Rate" *Brain Research*, 199:161-174 (12/1980).

(List continued on next page.)

OTHER PUBLICATIONS

Ames, et al., "Cerebral Ischemia: II. The Na-Reflow Phenomenon" Am. J. Pathol., vol. 52, No. 2, pp. 437–448 (12/1968).

Berkenbosch et al., "Influence of the CSF Bicarbonate Concentration on the Ventilatory Response to $CO_2$ in Relation to the Location of the Central Chemoreceptors" Respiration Physiology, 35:215–236 (12/1978).

Sklar, Frederick H. et al., "Recirculatory Spinal Subarachnoid Perfusions in Dogs: A Method for Determining CSF Dynamics Under Non-Steady State Conditions," Neurosurgery, vol. 1, No. 1, pp. 48–56 (2/1977).

Sloviter, Henry A. et al., "Erythrocyte Substitute for Perfusion of Brain," Nature, vol. 216, pp. 458–460 (Nov. 4, 1967).

Hansebout, Robert R. et al., "Oxygenated Fluorocarbon Perfusion as Treatment of Acute Spinal Cord Compression Injury in Dogs," J. Neurosurg., Vo. 55, pp. 725–732 (12/1981).

Geyer, et al., "9 Survival of Rats Totally Perfused with a Fluorocarbon-Detergent Preparation", Organ Perfusion and Preservation, pp. 85–96 (11/1968).

Glogar et al., "Fluorocarbons Reduce Myocardial Ischemic Damage after Coronary Occlusion", Science, vol. 211, pp. 1439–1441 (Mar., 1981).

Gould et al., "How Good are Fluorocarbon Emulsions as $O_2$ Carriers?" Departments of Surgery, Michael Reese Hospital et al., pp. 1–3, 3/81.

Fischer, E., "Impaired Perfusion Following Cerebrovascular Stasis, Arch. Neurol, Vo. 29, pp. 361–366 (Dec. 1973).

Fritschka, et al., "Total and Regional Cerebral Blood Flow During Perfusion from the Lateral Ventricle to the Cisterna Magna in Conscious Dog: Effect of Hemorrhagic Hypotension and Retransfusion on Cerebral Blood Flow" Circulatory Shock, 7:333–342, (12/1980).

Fritschka, et al., "Increased Free Fatty Acid Turnover in CSF During Hypotension in Dogs", American J. Physiology, V. 236, pp. H802–H807, (12/1979).

Grote, J., "Cerebral Oxygen Supply in Brain Edema and During Ventriculo-Cisternal Perfusion", Adv. in Exp. Med. Biol., vol. 75, pp. 313–324 (11/1975).

Heisey, et al., "Bulk Flow and Diffusion in the Cerebrospinal Fluid System of the Goat", American J. of Physic., vol. 203, pp. 775–781 (11/1962).

Hossmann, et al., "Cation Activities in Reversible Ischemia of the Cat Brain", Stroke, vol. 8, pp. 77–81 (11/1977).

Hossmann et al., "Resuscitation in the Monkey Brain after 1 H Complete Ischemia, 1, Physiological and Morphological Observations Brain Research, 81:59–74 (6/1974).

Hossmann et al., "Reversibility of Ischemic Brain Damage", Arch. Neurol., vol. 29, pp. 375–384 (Dec. 1973).

Javid, et al., "Hypothermic Ventricular Perfusion—Evaluation of use in Cerebrovascular Occlusion" New York State Journal of Medicine, pp. 248–251 (Jan. 15, 1967).

Kleihues, et al., "Purine Nucletide Metabolism in the Cat Brain after One Hour of Complete Ischemia", Journal of Neurochemistry, vol. 23, pp. 417–425 (6/1974).

Min-Chu Liew et al., "A Technique for Perfusing the Cerebrospinal Fluid Spaces of the Cat from Lateral Ventricle via the Cisterna Magna to the Cortical Subarachnoid Space", J. Physiol., pp. 20P–21P (Dec., 1977).

Martins, et al., "Sources of Error in Measuring Cerebrospinal Fluid Formation by Ventriculocisternal Perfusion", Journal of Neurosurgery and Psychiatry, Vo. 40, pp. 645–650, (6/1977).

Mizoi, et al., "Experimental Study of New Cerebral Protective Substances Functional Recovery of Severe, Incomplete Ischaemic Brain Lesions Pretreated with Mannitol and Fluorocarbon Emulsion Acta Neurochirurgica 56, pp. 157–166 (1981).

Peerless, et al., "Protective Effect of Fluosol-DA in Acute Cerebral Ischemia", Stroke, vol. 12, No. 5, pp. 558–563, (4/1981).

Reulen, et al., "Clearance of Edema Fluid into Cerebrospinal Fluid" J. Neurosurg. 48: 754–764 (4/1978).

Schutz, et al., "Brain Mitochondrial Function after Ischemia and Hypoxia", Arch. Neurol., vol. 29, pp. 417–419 (Dec. 1973).

Sokoll, et al., "Dibutyryl Cyclic Adenosine Monophosphate Effects in the Ischemic-Hypoxic Cat", Stroke, vol. 8, No. 3, pp. 371–373 (May–Jun., 1977).

J. Suzuki et al., Current Topics 9:465–479 (6/1981).

Tsuyumu, et al., "Dynamics of Formation and Resolution of Vasogenic Brain Oedema I. Measurement of Oedema Clearance into Ventricular CSF", Acta Neurochirurgica 57:1–13, (6/1981).

(List continued on next page.)

OTHER PUBLICATIONS

Tremper, et al., "The Preoperative Treatment of Severely Anemic Patients with a Perfluorochemical Blood Substitute, Fluosol-DA 20%", *Crit. Care Med.* 8, p. 738 (6/1980).

Weyne et al., "Restoration of CSF[HCO$_3$] after its Experimental Lowering in Normocapnic Conditions", *J. of Applied Physics*, V. 47, pp. 369-376 (Jul.-Sep. 1979).

Abstract No. [85] Pool Rounds (one page.).

Booklet "William Harvey Introduces a New Geometry for Oxygen Performance."

State of the Art Symposium "Artificial Blood", National Institutes of Health, Apr. 5-6, 1974, Federatoin Proceedings, vol. 34, No. 6, pp. 1428-1517 (6/1975).

Nordstrom et al., *Acta Physiol. Scand.* (6/1977).

Siezyo, et al., *Adv. Exp. Med. Biol.* 78;261-269 (5/1977).

Clark, et al., *Microvasc. Res.* 8:320-340 (4/1974).

S. A. Gould et al., *Fed. Proc.* 40:2038 (4/1981).

Doss, et al., Microvascular Research 13, pp. 253-260 (3/1977).

Osterholm, J., et al., "Severe Cerebral Ischemia Treatment by Ventriculosubarachnoid Perfusion with an Oxygenated Fluorocarbon Emulsion", *Neurosurgery*, vol. 13, No. 4, pp. 381-387 (2/1983).

News Release "Philadelphia Doctor Named Inventor of the Year; Developed Revolutionary System for Treatment of Stroke" *Intellectual Property Owners, Inc.*, Apr. 17, 1985.

Faithfull, N. S. et al., "Whole-Body Oxygenation Using Intraperitoneal Perfusion of Fluorocarbons", *British Journal of Anaesthesia*, 56;867 (4/1984).

Steadman's Medical Dictionary, Fifth Unabridged Layer's Edition, Anderson Publishing Co., Cincinnati and Jefferson Law Book Company, Washington, D.C. 12/1982, p. 1181.

Long et al., "Efficacy and Toxicity Studies with Radiopaque Perfluorocarbon", *Radiology*, 105(2):323-332 (Nov., 1972).

Long et al., "Initial Observations with a New X-Ray Contrast Agent—Radiopaque Perfluorocarbon", *Review of Surgery*, pp. 71-76 (Jan.-Feb., 1972).

*Textbook of Biochemistry with Clinical Correlations*, edited by Thomas M. Devlin, Ph.D., published by John Wiley & Sons, New York, 3/1982, pp. 268-277.

Perfluorochemical Blood Substitutes FC-43 Emulsion Fluosol-DA, 20% and 35% for Preclinical Studies as a Candidate for Erythrocyte Substitution, Naito et al., The Green Cross Corp., 7/86.

Supplement to Perfluorochemical Blood Substitutes FC-43 Emulsion Fluosol-DA, 20% and 35% as Oxygen Carrying Cooloidal Blood Substitute, Naito et al., The Green Cross Corp.

K. Yokoyama et al., "Development of Fluosol-DA and its Perspective as a Blood Substitute", Symp. 2nd Priestley Conf., Oxygen and Life (1980), published in Supplement to Perfluorochemical Blood Substitutes, The Green Cross Corporation, pp. 27-37.

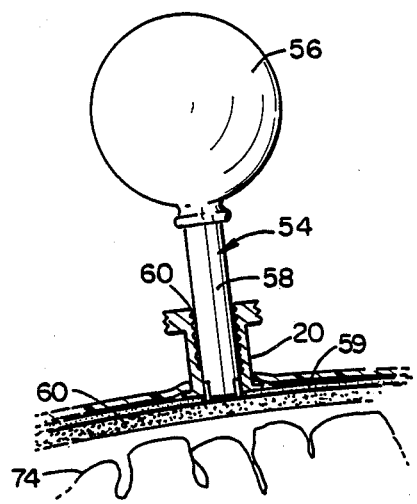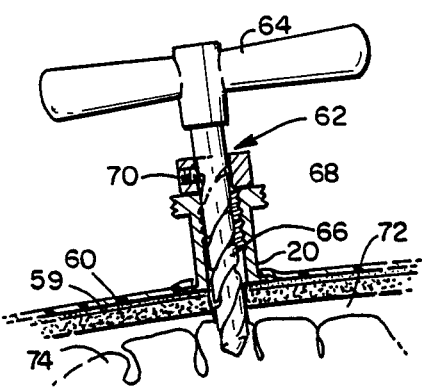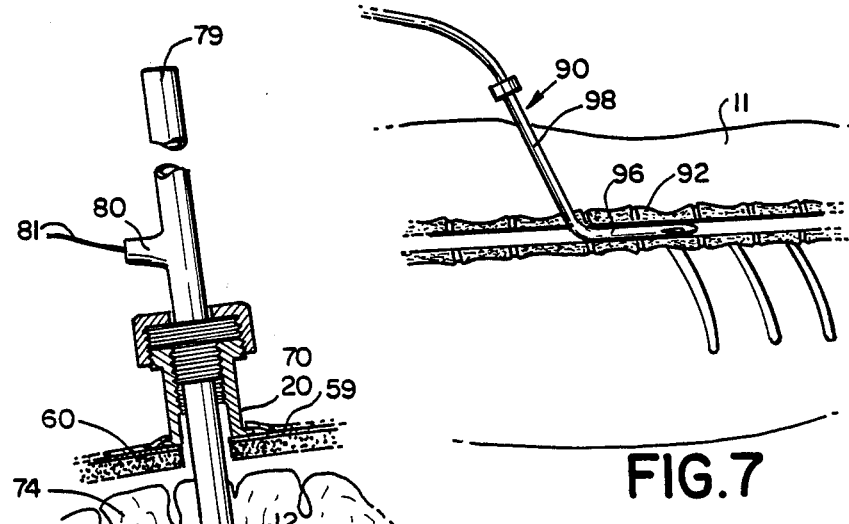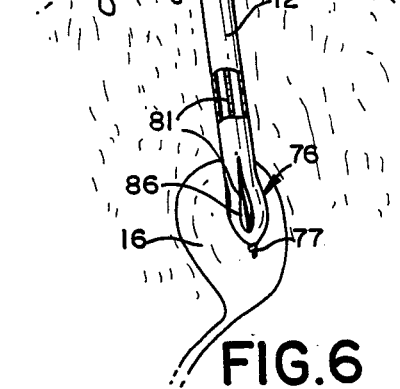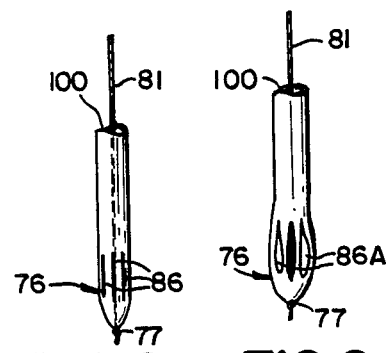

CEREBRAL AND LUMBAR PERFUSION CATHETERIZATION APPARATUS FOR USE IN TREATING HYPOXIC/ISCHEMIC NEUROLOGIC TISSUE

This is a continuation of application Ser. No. 755,427, filed July 16, 1985 now abandoned which is a continuation-in-part of Ser. Nos. 428,900, filed Sept. 30, 1982, U.S. Pat. No. 4,758,431 and Ser. No. 582,961, filed Feb. 23, 1984, U.S. Pat. No. 4,686,085. Ser. No. 582,961 is, in turn, a division of Ser. No. 428,850, filed Sept. 30, 1982, now U.S. Pat. No. 4,445,500 which along with Ser. No. 428,900 U.S. Pat. No. 4,758,431 are both, in turn divisions of Ser. No. 354,346, filed Mar. 3, 1982, now U.S. Pat. No. 4,445,886 and which in turn is a continuation-in-part of Ser. No. 139,886 filed Apr. 14, 1980, now U.S. Pat. No. 4,378,797.

FIELD OF THE INVENTION

This invention relates in general to cerebral and lumbar catheterization apparatus useful for the perfusion or drainage of fluids from the cerebral and spinal regions and, in particular, it relates to an apparatus particularly useful in treating hypoxic/ischemic neurologic tissue arising from cerebral vascular accident by allowing the circulation of oxygen carrying synthetic liquids through the neurologic tissue.

RELATED APPLICATIONS AND PATENTS

In addition, the present application is related to the following issued U.S. Patents, all of which are incorporated herein by reference as if set forth in full and all of which are divisions of one or the other of the aforementioned Ser. Nos. 139,886 and 354,346:

U.S. Pat. No. 4,445,514 entitled "Extra Vascular Circulation of Oxygenated Synthetic Nutrients to Treat Tissue Hypoxic and Ischemic Disorders";

U.S. Pat. No. 4,393,863, entitled "Extra Vascular Circulation of Oxygenated Synthetic Nutrients to Treat Tissue Hypoxic and Ischemic Disorders";

U.S. Pat. No. 4,450,841, entitled "Stroke Treatment Utilizing Extra Vascular Circulation of Oxygenated Synthetic Nutrients to Treat Tissue Hypoxic and Ischemic Disorders";

U.S. Pat. No. 4,445,887, entitled "Stroke Treatment Utilizing Extra Vascular Circulation of Oxygenated Synthetic Nutrients to Treat Tissue Hypoxic and Ischemic Disorders";

U.S. Pat. No. 4,446,154, entitled "Stroke Treatment Utilizing Extra Vascular Circulation of Oxygenated Synthetic Nutrients to Treat Tissue Hypoxic and Ischemic Disorders";

U.S. Pat. No. 4,446,155, entitled "Stroke Treatment Utilizing Extra Vascular Circulation of Oxygenated Synthetic Nutrients to Treat Tissue Hypoxic and Ischemic Disorders";

U.S. Pat. No. 4,451,251, entitled "Stroke Treatment Utilizing Extra Vascular Circulation of Oxygenated Synthetic Nutrients to Treat Tissue Hypoxic and Ischemic Disorders";

U.S. Pat. No. 4,445,888, entitled "Stroke Treatment Utilizing Extra Vascular Circulation of Oxygenated Synthetic Nutrients to Treat Tissue Hypoxic and Ischemic Disorders";

U.S. Pat. No. 4,445,500, entitled "Stroke Treatment Utilizing Extra Vascular Circulation of Oxygenated Synthetic Nutrients to Treat Tissue Hypoxic and Ischemic Disorders";

BACKGROUND OF THE INVENTION

Cerebral vascular accident, a disease commonly known as "stroke" remains the third leading cause of death, and probably constitutes the single largest category of long-term disability in this country. In spite of current medical knowledge and available treatments, a major central system vascular occlusion is quickly attended by irreversible damage to the affected brain region(s). A "completed stroke" is manifest by a fixed and permanent neurological deficit. Millions of dollars have been expended in stroke research and care by federal and private agencies without a single substantial gain in our present chemotherapeutic abilities for a completed stroke.

In each of the aforementioned patents and applications, however, the present applicant has disclosed and claimed a novel nutrient formulation for circulation through cerebro-spinal fluid pathways, and systems and methods for using the same to treat central nervous tissue hypoxic-ischemic conditions. Applicant has recognized that there is a therapeutic time window through which neurons can be reached and resuscitated.

In accordance with the inventions disclosed and claimed in the aforementioned patents and applications, a synthetic cerebro-spinal fluid is circulated through the cerebro-spinal fluid passageways immediately after a stroke. Specifically, the oxygenated nutrient is circulated through those cerebro-spinal fluid passageways which contact brain and spinal cord tissue. According to these methods, treated tissues exhibit a substantially improved ability to resist and/or repair damage which would otherwise result from vascular occlusion.

The circulation apparatus disclosed in the aforementioned patents and applications comprises a reservoir containing a nutrient emulsion; means for delivering the nutrient emulsion at preselected flow rates; an oxygenation means for equilibrating the nutrient emulsion to desired gaseous tension levels; heat exchanger and/or cooling unit means for selectively controlling the temperature of the nutrient emulsion; filter means for cleansing the nutrient emulsion; and circulation monitoring means for ensuring the desired circulation flows are maintained within the system. Specifically, in carrying out the method described and claimed in the aforementioned patents and applications, the nutrient emulsion is delivered from the nutrient emulsion reservoir to the lateral ventricle of the brain. Injection of the nutrient input stream directly to the brain permits the oxygenated nutrient emulsion to come into contact with the subarachnoid spaces, miniature Virchow-Robins spaces, cerebral and cord surfaces, and cerebral ventricles. Circulation of the nutrient input stream through at least a portion of the cerebro-spinal pathway may be accomplished by withdrawing fluid from the spinal subarachnoid space, or alternatively, from the cisterna magna.

While the aforementioned system and method have been found to be particularly useful in the treatment of stroke, treatment must be begun within a therapeutic time window immediately following the onset of the stroke. Because time is so critical, treatment must be administered by paramedics and emergency personnel or, alternatively, by emergency room physicians and staff. Since the treatment described in the aforementioned patents and applications requires the injection of oxygenated nutrient emulsion directly into the lateral ventricles of the human brain and the withdrawal of that nutrient emulsion from the subarachnoid space or the cisterna magna, it should be clear that the procedures used in the treatment are not ones which paramedics and emergency personnel or even most emergency room personnel are familiar with.

Specifically, the treatment requires that an aperture be formed in the cranium and that a catheter be inserted directly through the aperture of the skull and thereafter through the soft tissue of the brain into the lateral ventricles. Such techniques are difficult enough for skilled neurosurgeons and are typically beyond the ken of paramedical personnel.

SUMMARY OF THE INVENTION

It is an object of the present invention to provide a cerebral and lumbar perfusion catheterization apparatus for use in treating hypoxic/ischemic neurologic tissue which may be easily utilized by paramedics and by emergency room personnel.

It is a further object of the present invention to provide such a perfusion catheterization apparatus which may be utilized quickly and with utmost accuracy so that treatment may be begun as soon as possible after the onset of stroke symptoms.

To accomplish these results, a novel method and apparatus are provided for rapidly inserting a cerebral perfusion catheter into the lateral brain ventricle.

In accordance with the apparatus of the present invention a placement appliance for engaging the head is provided having guide means for receiving and directing a catheter to the lateral brain ventricle. The appliance accurately positions the guide means with respect to the head at a location offset from the center line. The guide means is a tubular structure having a threaded internal bore. The catheter further includes an external threaded portion mating with the internal threaded bore of the guide means such that when the catheter and guide means are mated, the insertion depth of the catheter may be precisely controlled by the rotational position of the catheter with respect to the guide means. A locking means is provided to ensure that once the catheter is inserted into the lateral ventricle, the position of the catheter vis-a-vis the guide means remains fixed during treatment so that the insertion depth does not vary during treatment.

In accordance with the method of the present invention, the aforementioned placement appliance having guide means is applied to the head o the patient such that the guide means are positioned at a location offset from the center line of the head, with the center line of the bore of the aforementioned guide means being directed toward the lateral ventricles. An aperture is created through the skull at the location of the guide means and thereafter the catheter is inserted through the guide means and the skull using the guide means to direct the catheter toward the lateral brain ventricle.

BRIEF DESCRIPTION OF THE DRAWINGS

The present invention will be more fully understood by reference to the accompanying drawings, in which:

FIG. 4 is a partial cross-sectional view through the cerebral catheterization apparatus shown in FIG. 3 along section lines 4—4, but with an obturator situated within the guide means thereof;

FIG. 5 is a cross-sectional view similar to that shown in FIG. 4, but with a drill means situated within the guide means thereof;

FIG. 6 is a cross-sectional view similar to that shown in FIG. 4, but with the catheter means of the present invention situated within the guide means, the catheter having a tip portion of a first configuration;

FIG. 7 is a schematic view of a lumbar catheterization apparatus useful in connection with the cerebral catheterization apparatus of the present invention;

FIG. 8 illustrates the tip of both the cerebral and the lumbar catheter means of the present invention in a first position suitable for insertion; and FIG. 9 illustrates the tip of both the cerebral and the lumbar catheter means of the present invention but in a second position after insertion.

DETAILED DESCRIPTION OF THE PREFERRED EMBODIMENTS

In the following more detailed description of the present invention, numerous examples have been selected for the purpose of explanation and illustration of the preferred embodiment. One of ordinary skill in the art will readily recognize that numerous substitutions or alterations from the embodiment set forth may be made without departing from the spirit of the present invention, which is defined by more particularly in the appended claims.

Figure 1:
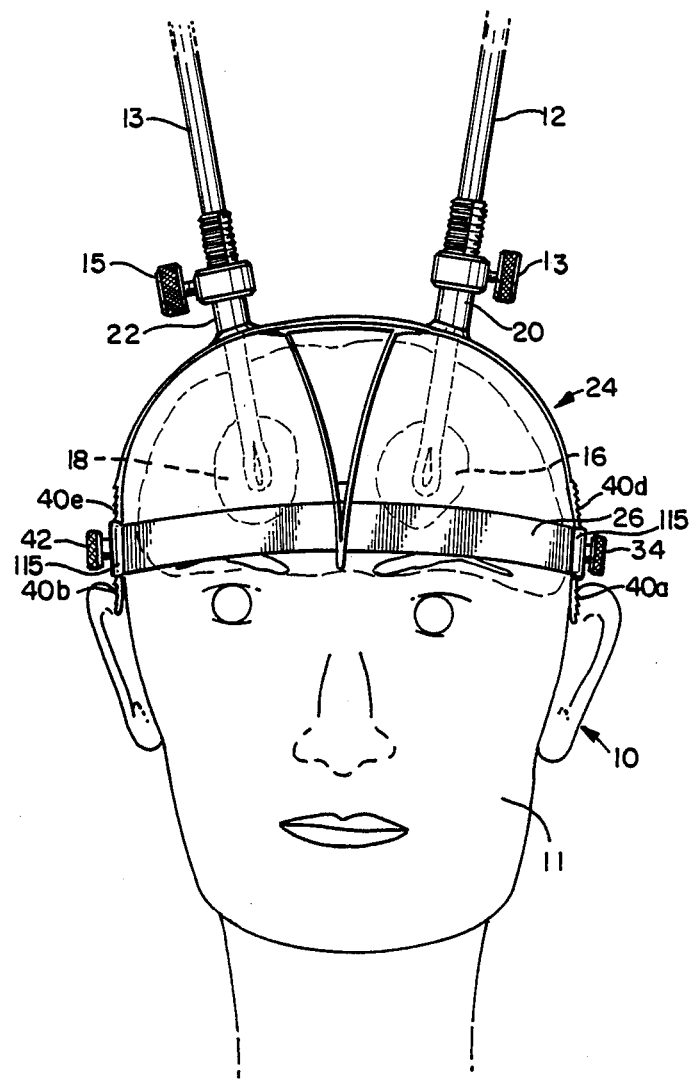
FIG. 1 is a frontal view of a patient wearing a cerebral catheterization apparatus in accordance with the present invention.

Referring now to FIG. 1, the cerebral catheterization apparatus of the present invention is shown generally at 10. The cerebral catheterization apparatus 10 is shown fitted on to a patient 11. The apparatus 10 is utilized for reliably inserting a cerebral perfusion catheter means 12 and 13 to the left and right lateral brain ventricles 16 and 18 of the patient 11. As shown in FIG. 1, the cerebral catheterization apparatus 10 includes an appliance for engaging the head having guide means shown generally at 20 and 22 for receiving and directing the catheter means 12 and 13.

Figure 2:
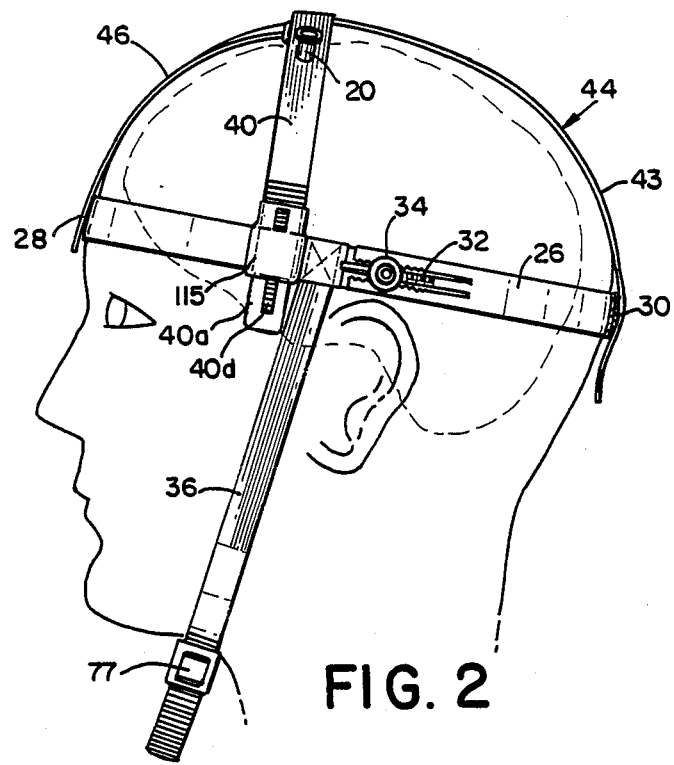
FIG. 2 is a side or lateral view of the patient wearing the cerebral catheterization apparatus of FIG. 1, but with the catheter means removed therefrom.

In order that the guide means 20 and 22 may be quickly and reliably positioned with respect to the left and right lateral brain ventricles 16 and 18 by emergency personnel, the guide means 20 and 22 are affixed to a harness 24 which accurately positions them with respect to the head of the patient 11. The harness 24 includes a horizontal strap 26 which is positioned about the head slightly above the ears and eyebrows. As best seen in FIG. 2, therefore, the horizontal strap 26 is positioned adjacent the forehead 28 at the anterior portion of the head and is positioned adjacent the occipital protuberance 30 at the posterior portion of the head The horizontal strap 26 is thus positioned with respect to the head such that the vertex of the skull is located above the strap. The horizontal strap 26 includes a fastening means 32 which preferably includes a thumb screws 34 and 42 permitting the circumferential size of the horizontal strap 26 t be adjusted depending on the head size of the patient 11. When fitted on a patient, the horizontal strap is adjusted using both of these screws to take up the same amount of strap slack, thereby establishing (bilateral) symmetry of the head to the apparatus 10.

The harness 24 further includes chin straps, one of which is shown at 36, for maintaining the horizontal strap 26 in a fixed position with respect to the head. The chin straps are affixed to the horizontal strap 26 on the left and right sides of the head of the patient 11. The chin straps are joined by a buckle or other fastening means beneath the chin. The harness 24 further includes a vertical transverse strap 40 which is also affixed to the horizontal strap 28 and to which the guide means 20 and 22 are affixed. Like the horizontal strap 26, the vertical transverse strap 40 also includes adjustment means, such as racheted slides, to accommodate varying head sizes. This may be accomplished by providing indicia on each tounge 40c of the strap 40 which indicate its position relative to its strap guide 115 which is attached to the horizontal strap 28. The tounges 40a and 40g may have rachet racks 40d and 40e protruding from one surface thereof, to selectively engage complimentally formed protrusions or teeth on the strap guides 115. This engagement permits rapid adjustment of the strap 40, but holds it firmly in place once properly positioned. The vertical transverse strap 40 is generally positioned parallel to and lies directly above the coronal suture, i.e., the juncture between the frontal and parietal skull bones.

Figure 3:
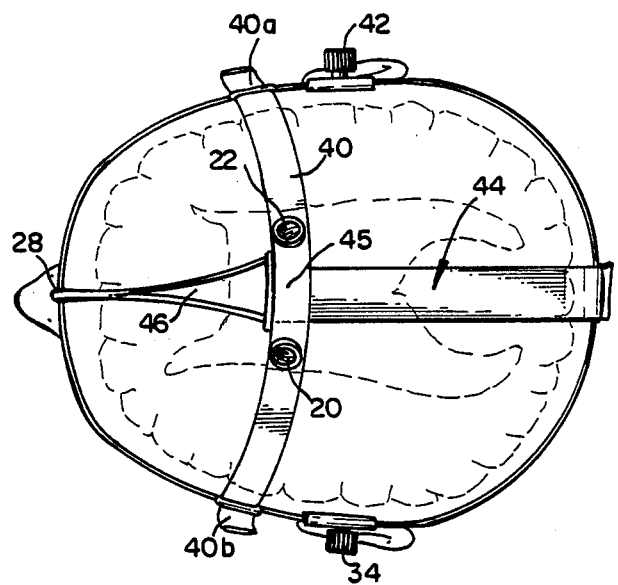
FIG. 3 is a top view of the patient and cerebral catheterization apparatus shown in FIG. 2.

As may best be seen in FIG. 3, also joined to the horizontal strap 26 is a vertical medial strap shown generally at 44. The vertical medial strap 44 includes a first or anterior portion 46 which joins the horizontal strap 26 in the vicinity of the forehead at 28 and a second or posterior portion 48 which joins with the horizontal strap 26 in the vicinity of the occipital protuberance 30. The first or anterior portion 46 and the second or posterior portion 48 of the vertical medial strap 44 join with the vertical transverse strap 40 in a position 45 which is intermediate the guide means 20 and 22. Such a position lies roughly over the bregma, i.e., the juncture between the coronal and saggital sutures of the skull. The vertical medial strap 44 is effective in appropriately positioning the guide means 20 and 22 in the anterior-to-posterior direction over the bregma.

Once the harness 24 and, therefore, the guide means 20 and 22 are appropriately positioned with respect to the head of patient 11, treatment is begun immediately. Referring now to FIGS. 4-6, the method of utilizing the cerebral catheterization apparatus 10 of the present invention in the course of such treatment will be described in further detail. After the positioning harness 24 described in connection with FIGS. 1-3 is located with respect to the head of the patient and the guide means 20 and 22 are positioned in the appropriate location with respect to the lateral ventricles 16 and 18 as described above, apertures are created through the skull at the position of the guide means 20 and 22. These apertures are formed in the skull 60 by means of an obturator 54 as shown in FIG. 4. The obturator 54 includes a handle portion 56 and an elongated stem portion 58 having an outside diameter fitting within the threaded internal bore 60 of the respective guide means 20 or 22. The obturator 54 is utilized to pierce the scalp 59 of the patient and to remove a core of that scalp so as to expose the underlying skull 60. After the core has been removed and the skull 60 has been exposed, the obturator 54 is removed from the guide means 20 or 22 as the case may be an the next step of the present method may begin.

This next step is shown in FIG. 5 in which a drill means 62 is shown. The drill means 62 includes a handle portion 64 and a downwardly extending drill bit 66. In accordance with the preferred embodiment of the present invention, the drill means further includes a stop 68 concentrically located about the outer periphery of the drill bit 66 and fixed with respect to the drill bit 66 by means of a set screw 70. Operation of the handle portion 64 of the drill means 62 causes an aperture to be formed in the skull 60 as will a in the underlying pia layer 72. The stop means 68 is provided to prevent the insertion of the drill bit 66 into an unnecessarily large portion of soft brain tissue 74. When the drill bit 66 is inserted to the appropriate depth, the stop means 68 abuts the upper surface of the guide means 20 or 22 as shown in FIG. 5 to control the insertion depth.

After the scalp 58 has been pierced and an aperture has been formed in the skull 60, the drill means 62 is removed from the guide means 20 and the third and next step of the present method may begin.

In this next step, a catheter means such as shown at 12 in FIG. 6, is inserted into the threaded internal bore 60 of the guide means 20 or 22. The catheter means 12 includes a tip portion 76 which is inserted into the lateral ventricle such as shown at 16 in FIG. 6. With the insertion of the catheter tip 76 into the lateral ventricle, treatment in accordance with the aforementioned patents and patent applications may begin and nutrient emulsion may be circulated through the ventricle.

In accordance with an important aspect of the present invention, the catheter means 12 includes a threaded external portion 78 which mates with and which is threadedly engaged with respect to the threaded internal bore 60 of the guide means 20 or 22 and external indicia which indicate the depth of insertion. The rotational position of the catheter means 12 with respect to the guide means 20 thus controls and provides a visual indication of the insertion depth of the catheter means 12. The proper insertion depth is determined by reference to the aforementioned indicia on the tongues 40a and 40b of the vertical strap 40. These indicia are scales to correspond to indicia on the catheter means so that the catheter insertion distance can be read from tongues 40a and/or 40b. This is possible due to the precise placement of the horizontal and vertical straps in the harness, and their known relative positions with respect to the lateral ventricles. It is therefore unnecessary for the user to have any particular knowledge of brain anatomy in order to properly insert the catheter once the harness is properly positioned. When the catheter means 12 is at the proper insertion depth, thumb screws 13 and 15 (FIG. 1) may be tightened so as to fix the catheter means 12 at the appropriate depth.

In accordance with another aspect of the present invention, the catheter means 12 and 14 each include a first port 79 through which nutrient emulsion is caused to flow and a second or pressure measurement port 80 through which intracranial pressure is monitored. Also passing through the pressure measurement port 80 is a wire means 81 which is coupled to the extreme end 77 of the catheter tip 76 for reasons which will become apparent below. The catheter means 12 is preferably made of semi-malleable plastic and is provided with multiple slit ports 86 at the tip 76 thereof. The slit ports 86 are spaced about the peripheral wall of the tip 76 of the catheter means 12.

To complete the treatment of the present invention, it is necessary that the nutrient emulsion which is inserted into the lateral brain ventricles be removed from the spinal subarachnoid space or, alternatively, from the cisterna magna. In order to facilitate removal of the nutrient emulsion from the subarachnoid space an improved lumbar catheter is described in connection with FIG. 7. As shown in FIG. 7, a lumbar catheter shown generally at 90 is inserted into the spinal column 92 of the patient 11. The lumbar catheter 90 includes a tip portion 96 and a body portion 98. The lumbar catheter 90 is made of semi-malleable plastic and is flexible at least at its inserted tip portion 96 so as to bend and protrude from the subarachnoid space of the spinal column 92 and project through the body wall. The lumbar catheter 90 is inserted into the subarachnoid space by first inserting a knife cannula into a hollow tube and using it to penetrate the skin, muscle and dura. When the tip of the knife and hollow tube are inserted into the subarachnoid space, the knife is withdrawn and the catheter is inserted into the hollow tube.

As shown in FIGS. 8 and 9 and in accordance with an important aspect of the present invention, both the cerebral catheters 12 and 14 and the lumbar catheter 90 include a thin wire 81 traversing through the central bore 100 thereof. The thin wire 84 is fixed to the extreme end portion 77 of the catheter means. As mentioned above and as shown in FIGS. 8 and 9, peripheral slit ports 86 are provided around the peripheral surface of the catheter tip 76. As shown in FIG. 8, the catheter tip 76 is initially in an undeformed position and the peripheral slits 86 are closed, thus making insertion of the catheter means relatively simple. After the catheter tip 76 has been inserted, the central wire 81 is moved to a retracted position, thus deforming the catheter tip 76 and expending the radial dimension of the catheter tip 76 as shown in FIG. 9. Such a result has the effect of expanding the slits 86 and transforming them to the more enlarged apertures 86A shown in FIG. 9. Such a result improves the flow of fluid emulsion both into and from the catheter means 12 or 90 as the case may be.

While a particular embodiment of the present invention has been shown and described, it will be appreciated that other embodiments may occur to those skilled in the art and such other embodiments come within the spirit and scope of the appended claims.

What is claimed is:

1. A cerebral catheterization apparatus for delivering oxygenated nutrient to or from the cerebro-spinal fluid pathway of a patient suspected of suffering from ischemic central nervous system tissue comprising:
    (a) catheter means for providing a delivery pathway for said oxygenated nutrient to the lateral ventricle of the brain of said patient, said delivery pathway comprising an inlet and outlet;
    (b) guide means, mating with said catheter means, for directing said catheter means toward said lateral ventricle; and
    (c) a harness, positionable with respect to the head of the patient, said guide means being mounted thereon, for positioning said guide means with respect to the head such that said catheter means may be reliably inserted into said lateral ventricle, said harness comprising:
        (i) a horizontal strap for encircling the head of the patient, the ventrex of the skull being above said horizontal strap; and
        (ii) a transverse strap coupled to said horizontal strap, said transverse strap generally lying above the coronal suture of said patient and lying in a generally vertical plane which intersects with the lateral ventricles, to thereby position said guide means at a predetermined location with respect to said ventricles, said guide means being mounted on said transverse strap.

2. The catheterization apparatus of claim 1 wherein said catheter means further comprises:
    a tube having a tip portion, said tip portion having a plurality of outlet openings therein for perfusing said oxygenated nutrient.

3. The catheterization apparatus of claim 1 wherein said tube further includes a threaded portion about at least a portion of the periphery thereof and wherein said catheter means further comprises:
    a mounting having a threaded internal bore mating with said threaded portion of said tube, the rotational position of said catheter means with respect to said guide means controlling the insertion depth of said catheter means into said ventricle.

4. The catheterization apparatus of claim 3 wherein said guide means further comprises:
    a locking means coupled to said mounting for selectively fixing the position of said catheter means with respect to said guide means.

5. The catheterization apparatus of claim 1 wherein said catheter means further comprises:
    a tube having an internal passageway and a tip portion, said tip portion being formed of semi-malleable plastic;
    a plurality of normally closed outlet slits situated about the periphery of said tip portion; and
    a wire means coupled to said tip portion and traversing said passageway for deforming said tip portion and for opening said outlet slits to form outlet openings through which said oxygenated nutrient flows when said wire means is in a retracted position.

6. The catheterization apparatus of claim 1 wherein said guide means further comprises:
    a mounting having an internal bore, said catheter means being insertable therein; and
    locking means coupled to said mounting for selectively fixing the position of said catheter means with respect to said guide means to control the insertion depth of said catheter means into said ventricle.

7. The catheterization apparatus of claim 1 wherein said catheter means comprises catheter depth insertion indicia for indicating the depth of insertion of said catheter.

8. The catheterization apparatus of claim 1 wherein said harness further comprises:
    at least one chin strap coupled to said horizontal strap for restraining the horizontal strap in a fixed position with respect to the head.

9. The catheterization apparatus of claim 1 wherein said harness further comprises:
    a vertical medial strap coupled to said horizontal strap in an anterior location and in a posterior location and further coupled to said transverse strap for restraining said transverse strap in an appropriate anterior-to-posterior position above the coronal suture.

10. The catheterization apparatus of claim 9 wherein the vertical medial strap is coupled to said vertical transverse strap at a point generally above the bregma of the patient.

11. The catheterization apparatus of claim 10 wherein said guide means is mounted to said vertical transverse strap at a position approximately 2 cm. from said point.

12. The catheterization apparatus of claim 1 wherein said vertical strap comprises adjustment indicia to indicate its relative position to said horizontal strap.

13. The catheterization apparatus of claim 12 wherein said indicia indicate the depth of required insertion of said catheter means for location of its tip in a lateral ventricle.

14. An apparatus for rapidly inserting a cerebral delivery catheter means into the lateral brain ventricle of a patient, said catheter means having an inlet and outlet, comprising:
   an appliance for engaging the head said appliance comprising a harness having a horizontal strap positionable about the horizontal surface of the skull, the vertex of the skull being above the horizontal strap, said appliance further comprising a transverse strap, said transverse strap being coupled to said horizontal strap;
   guide means mounted on said transverse strap for receiving and directing said catheter means to the lateral brain ventricle;
   said transverse strap being positionable to lie in a generally vertical plane which intersects with the lateral ventricles, to thereby position said guide means at a predetermined location with respect to said ventricles; and
   a catheter means mating with said guide means such that when said character and guide means are mated the insertion position of said catheter with respect to the head is controlled.

15. The apparatus of claim 14 wherein said guide means comprises:
   a tubular structure having a threaded internal bore; and wherein
   said catheter means includes a threaded external portion mating with the threaded internal bore of said guide means such that the insertion depth of said catheter may be controlled.

16. A method of rapidly inserting a cerebral delivery catheter means into a lateral brain ventricle of a patient, said catheter means having an inlet and outlet comprising:
   (a) providing an appliance for engaging the head of the patient, said appliance having guide means for receiving and directing said catheter and comprising a harness having a horizontal strap positionable about the horizontal circumstance of the skull and a transverse strap coupled to said horizontal strap;
   (b) locating said appliance with respect to the head to position by locating the horizontal strap below the vertex of the skull around the maximum horizontal circumference of the skull and adjusting the horizontal and transverse strap to positions such that the transverse strap lies in a generally vertical plane which intersects with the lateral ventricles, to thereby position the guide means at a predetermined location with respect to said ventricles;
   (c) creating an aperture through the skull at the location of said guide means;
   (d) inserting said catheter means through said aperture using said guide means to direct said catheter means towards a lateral brain ventricle until a portion of said catheter means is disposed within that ventricle.

17. The method of claim 16 wherein said predetermined location is about 2 cm from the medial center line of said skull.

18. The method of claim 17 wherein said predetermined location is about 2 cm from the medial center line of the head generally above the coronal suture.

19. The method of claim 18 wherein said guide means is directed approximately perpendicular to a tangent of the skull at said predetermined location.

20. The method of claim 16 wherein said position lies generally above the coronal suture.

21. The method of claim 16 wherein said catheter means comprises an externally threaded portion and said guide means comprises an internal threaded portion mating therewith and wherein said inserting step further comprises:
   coupling said catheter means to said guide means;
   rotating the external threaded portion of said catheter means with respect to the internal threaded portion of said guide means so as to adjust the insertion depth of said catheter means; and
   fixing said catheter with respect to said guide means when said catheter is at a proper insertion depth.

* * * * *